United States Patent

Mayes et al.

[11] Patent Number: 5,948,930
[45] Date of Patent: *Sep. 7, 1999

[54] PROCESS FOR PREPARING O-ALKYL, O-ALKYLPHOSPHOROCHLORIDOTHIOATES

[75] Inventors: David M. Mayes, Overland Park, Kans.; Daniel M. Wasleski, Raytown, Mo.; Gerd Grah, Haan; Hermann Seifert, Bergisch Gladbach, both of Germany

[73] Assignees: Bayer Corporation, Pittsburgh, Pa.; Bayer Aktiengesellschaft, Leverkusen, Germany

[*] Notice: This patent issued on a continued prosecution application filed under 37 CFR 1.53(d), and is subject to the twenty year patent term provisions of 35 U.S.C. 154(a)(2).

[21] Appl. No.: 08/927,850

[22] Filed: Sep. 11, 1997

[51] Int. Cl.$^6$ ............................................. C07F 9/16
[52] U.S. Cl. ................... 558/90; 558/92; 558/99; 558/100
[58] Field of Search ................. 558/90, 92, 99, 558/100

[56] References Cited

U.S. PATENT DOCUMENTS 3,365,532  1/1968  Kauer .
3,790,649  2/1974  Schumacher et al. .................. 260/973
4,127,652  11/1978  Maurer et al. .......................... 424/200
4,666,894  5/1987  Maurer et al. ............................ 514/86

OTHER PUBLICATIONS

Organic Phosphorous Compounds, vol. 7 (month unavailable) 1976, pp. 500–502.

Beilstein on stn on line–Beilstein registry No. 471486, a mixed alkyl ester, disclosed in Zh Obshch Kim 27 p. 1908, 1957.

Chemical abs vol. 63, 17875h, abs of "Cyclic organophosphorus compounds." Tetrahedron 21(9), pp. 2379–2387, 1965.

*Primary Examiner*—Gary Geist
*Assistant Examiner*—Jean F Vollano
*Attorney, Agent, or Firm*—Joseph C. Gil; Carol Marmo

[57] ABSTRACT

The invention relates to process for the preparation of an O-alkyl, O-alkyl phosphorochloridothioate by 1) reacting A) a thiophosphoryl halide with B) an alcohol, in the presence of C) a tertiary amine acid acceptor and D) a solvent, and 2) reacting the resultant product with a second alcohol, different from the alcohol used in step 1). In the preferred embodiment, the intermediate product is not isolated before reaction with the second alcohol.

10 Claims, No Drawings

PROCESS FOR PREPARING O-ALKYL, O-ALKYLPHOSPHOROCHLORIDOTHIOATES

BACKGROUND OF THE INVENTION

O-alkyl,O-alkyl phosphorochloridothioates are known intermediates for the production of pesticides (see, e.g., U.S. Pat. Nos. 4,127,652 and 4,666,894).

The reaction of thiophosphoryl chloride with an alcohol to produce an O-alkylphosphorodichloridothioate is known. In addition, the reaction of an O-alkylphosphorodichloridothioates with an alcohol to produce an O-alkyl,O-alkyl phosphorochloridothioate is also known. It is also known that these processes can be carried out in the presence of tertiary amines. These two reaction schemes are broadly described in ORGANIC PHOSPHOROUS COMPOUNDS, Volume 7 (1976), pages 500–502 (see also, U.S. Pat. No. 3,790,649). When tertiary amines are used, solid HCI salts of the tertiary amines are formed. These salts typically require the use of significant amounts of solvent in order to allow the salts to be slurried and/or solubilized.

The invention provides an improved process for preparing O-alkyl,O-alkyl phosphorochloridothioates at acceptable reaction rates, purity and yield, without the need to use large amounts of solvent. In the most preferred embodiment, the intermediate product is not isolated.

DESCRIPTION OF THE INVENTION

The present invention is directed to a process for the preparation of an O-alkyl,O-alkyl phosphorochloridothioate comprising:

1) reacting A) a thiophosphoryl halide with B) an alcohol, in the presence of C) a tertiary amine acid acceptor selected from the group consisting of tertiary pyridine bases, tertiary pyrrolidine bases and tertiary pyrrolle bases, and D) a solvent, wherein the relative amounts of materials are as follows:
   i) the weight ratio of (D) to (A) is from 1:0.25 to 1:5,
   ii) the molar ratio of (C) to (A) is from 1.5:1 to 5:1, and
   iii) the molar ratio of (A) to (B) is from 1:1 to 1:2,
2) reacting the resultant product with a second alcohol, different from the alcohol used in step 1), wherein the molar ratio of said second alcohol to said thiophosphoryl halide is from 1.5:1 to 5:1.

The present invention is directed to a process comprising first reacting a thiophosphoryl halide (such as thiophosphoryl chloride or thiophosphoryl bromide) with an alcohol which is a primary or secondary alcohol in a solvent, in the presence of a tertiary amine acid acceptor in an effective amount which forms a soluble salt in the reaction medium, followed by reacting the resulting intermediate product with a second alcohol which is a primary alcohol or secondary alcohol that is different from the alcohol of the initial step. In the most preferred embodiment, the intermediate product is not isolated.

It is a distinct feature of the invention that substantially all of the acid acceptor that is used herein can be recovered and recycled. It is further a distinct feature of the invention that, in the most preferred embodiment, since there is no isolation of the intermediate product, the same acid is used in both steps of the reaction. It is furthermore a distinct feature of the invention that small amounts of solvents are used in the process of the invention. Hence, large amounts of solvents are not required for slurry dilution of the resultant acid acceptor salt. In the first step of the process of the invention a thiophosphoryl halide such as thiophosphoryl chloride or the equivalent thereof is reacted in a solvent with a first alcohol such as isopropanol in the presence of an effective amount of a tertiary amine acid acceptor (selected from the group consisting of tertiary pyridine bases, tertiary pyrrolidine bases and tertiary pyrolle bases) to produce a thiophosphoric acid ester dichloride.

The volumetric efficiency of the first reaction step can be improved by reducing the solvent concentration. By volumetric efficiency is meant the ratio of product produced per unit volume. In accordance with the invention, one can conduct the reaction in a solvent concentration of about 10–20 percent by volume of the reactor. In contrast, art related reactions would typically be conducted in a solvent concentration of about 30–40 percent of the reactor. In the art-related process, the solvent concentration required during the reaction is determined by the ability to suspend the solid amine.

The solvent is employed in relatively small amounts. Typically, the weight ratio of solvent to thiophosphoryl halide is from 1:0.25 to 1:5, and is preferably from 1:1 to 1.5:1. The overall production rate of the reaction is improved by the volumetric efficiency of the reaction. Furthermore, with less solvent to recover and recycle, the entire production process becomes volumetrically more efficient.

The thiophosphoryl halides useful herein are generally known in the art. Illustrative of the thiophosphoryl halide are thiophosphoryl chloride and thiophosphoryl bromide, with the chloride being preferred.

The first alcohol is an alkyl alcohol having from 1 to 6 carbon atoms. Specific examples include isopropyl alcohol, n-propyl alcohol, ethanol, methanol and butanol. Isopropyl alcohol is the preferred alcohol to be used in the first step of the process.

The tertiary amine acid acceptors useful herein are selected from the group selected from the group consisting of tertiary pyridine bases, tertiary pyrrolidine bases and tertiary pyrolle bases. Such bases do not contain any available protons. Examples of tertiary pyridine bases include pyridine; 2-, 3- or 4-methylpyridine; 2,4- or 2,6-dimethylpyridine; 2- or 4-ethylpyridine; 5-ethyl- or 4-ethyl-2-methylpyridine; 4-phenylpropylpyridine; 2,4,6-trimethylpyridine; quinoline; isoquinoline; 2-, 4- or 6methylquinoline; and the like. Examples of a tertiary pyrrolidine bases include N-alkyl pyrrolidines such as N-methylpyrrolidine. Examples of tertiary pyrolle bases is N-alkylpyrroles such as N-methylpyrrole. The presently preferred amine are 5-ethyl-and 4-ethyl-2-methylpyridine.

The molar ratio of the amine acid acceptor to the thiophosphoryl halide is from about 1.5:1 to 5:1 and preferably from 2.5:1 to 3.5:1.

Solvents useful herein include aliphatic hydrocarbons such as pentane, hexane, heptane, cyclohexane and isooctane; aromatic hydrocarbons such as benzene, toluene, xylene, mesitylene, and cumene; and inactive ketones such as methylisobutyl ketone. Aromatic solvents are preferred, with toluene being most preferred.

The molar ratio of thiophosphoryl halide to first alcohol is from about 1:1 to 1:2. The first reaction can be conducted at a temperature of from −10 to 50° C. and preferably −10 to 30° C.

The resulting reaction product comprises an O-alkyl, phosphorodichloridothioate and is subjected to the second step of the process. In the second step, the intermediate reaction product is reacted with the second alcohol. The second alcohol is different from the first alcohol and also is an alkyl alcohol having from 1 to 6 carbon atoms. Specific examples include isopropyl alcohol, n-propyl alcohol, ethanol, methanol and butanol. When isopropyl alcohol is the first alcohol, ethanol is the preferred alcohol. to be used in the second step of the process.

The molar ratio of starting thiophosphoryl halide to the second alcohol is from about 1:1.5 to 1:5 of the thiophosphoric acid halide to the second alcohol can be employed. This reaction can be conducted at a temperature of about −10 to 50 C. and preferably 0 to 20° C.

The most preferred embodiment avoids isolation of the intermediate product. Combining the first and second steps of the reaction is accomplished by harnessing the solubility characteristics of the acid acceptor salt. More specifically, the first step can be combined with the second step (i.e., without isolation) by providing an acid acceptor salt that is soluble in the reaction system. By "reaction system" is meant the solvent, reactants and reaction products present.

The sequential reaction process is volumetrically more efficient than the processes noted earlier, by virtue of employing the first step described above. As would be realized, because less solvent is required, more of the reactants can be employed in the first and/or second step of the reaction. Moreover, the use of less solvent eliminates the need to isolate the intermediate reaction product before the second step reaction. In contrast, as noted above, the prior art required relatively large quantities of solvent. This necessarily reduced the volume available for reactants to such an extent that it was impractical to conduct the sequential reaction without isolating the intermediate reaction product. The prior art multiple step process would employ the solvent at a level higher of from 30 to 40 percent of the reactor volume. In accordance with the invention, the multi-step process can employ the solvent at a level of from about 10 to 20 percent of the reactor volume.

The success of the process of the present invention depends upon using an abnormally high excess of the alcohol in the second step. This certainly would not apparent or predictable form the prior art.

The process according to the invention requires easily accessible starting materials to produce the desired products in good yield and purity. The O,O-dialkylphosphorochloridothioate obtainable in accordance with the process can be isolated from the reaction mixture by relatively simple operations. For example, after the reaction of the second alcohol is complete, the reaction mixture is drowned in an hydrochloric acid solution. In general, the pH of the mixture (i.e., reaction mixture and acid solution) should be kept below 3 to ensure that the tertiary amine is converted to the corresponding HCl salt. The resultant aqueous phase is removed via phase separation. The organic phase, which contains the desired O,O-dialkylphosphorochloridothioate, is washed with dilute HCl to remove any traces of the tertiary amine. The product can then be dried.

A further feature of the invention is that the process does not pollute the environment. The aqueous phase from the dilute acid wash is combined with the drown water. Residual alcohol is first stripped from the mixture. Once the removal is complete, caustic is added to raise the pH to convert the tertiary amine HCl salt to tertiary amine and salt. The tertiary amine can then be readily separated. The tertiary amine acid acceptors can thus be employed repeatedly, so that it is not necessary to discharge them from the process after they have been used once.

By the process of the present invention, one can produce O,O-dialkylchlorothiophosphate such as O-ethyl, O-isopropylphosphorochloridothioate at good production rates, purity and yield, even without isolating the intermediate product. This product may be used as an intermediate for the synthesis of pesticides.

The invention is further illustrated but is not intended to be limited by the following examples in which all parts and percentages are by weight unless otherwise specified.

EXAMPLES

Example 1

181.7 g (1.5 moles) of 4-ethyl-2-methylpyridine are added over the course of 10 minutes to a solution of 196.5 g (1.0 mole) of thiophosphoryl chloride and 450 g of toluene at −5° C. 66 g (1.1 moles) of isopropanol are then metered into the mixture over the course of one hour, and the mixture is stirred at −5° C. for one hour. The resulting suspension is warmed to 20° C. and stirred for a further 3 hours at 20° C. With gentle cooling, 318.5 g (0.55 mole) of 6.3% strength hydrochloric acid are added at 20° C. The 2 phases which form are separated, and the aqueous pyridine HCl phase is extracted with 50 g of toluene. The organic product is purified by extracting with 50 g of water and then dried by partial distillation in vacuo down to 30 mbar.

This results in 627 g (0.897 mole) of 27.6% strength O-isopropyl dichlorothiophosphate solution in toluene in a yield of 89.7%.

This solution is used without further workup for the next reaction stage (O-isopropyl O-ethyl chlorothiophosphate).

181.7 g (1.5 moles) of 2-methyl4-ethylpyridine are added over the course of 10 minutes to a 627 g (0.897 mole) of 27.6% strength O-isopropyl dichlorothiophosphate solution in toluene from the previous stage present in the reactor at 20° C. Then 138.2 g (3.0 moles) of ethanol are metered in at 25° C. over the course of 30 minutes, and the mixture is stirred for 6 hours. Then, with gentle cooling, 387 g (0.67 mole) of 6.3% strength hydrochloric acid at added at 20° C. The 2 phases which form are separated, and the lower aqueous pyridine HCl phase is extracted with 50 g of toluene. The organic product phase is purified by extracting with 50 g of water and then dried by partial distillation in vacuo down to 30 mbar.

This results in 595 g (0.81 mole) of 27.6% strength O-isopropyl O-ethyl-phosphorochloridothioate solution in toluene in a yield of 90.3%.

A subsequent short-path distillation removes further toluene, and then the ester is distilled in a thin-film evaporator in vacuo at 45–50° C. This results in 162 g of distillate containing 88.8% (0.71 mole) of O-isopropyl O-ethyl-phosphorochloridothioate (4.7% other compounds, 6.5% toluene). The yield is 79.2%.

This product can be used directly for synthesizing the required O,O'-dialkyl O'''-aryl (or heteroaryl) esters.

Example 2

Recovery of 2-methyl4-ethylpyridine 317 g (3.57 mole) of 45% strength sodium hydroxide solution were added to 1151 g of 41% strength methyethylpyridine HCl solution (aqueous phases from the preparation of the mono- and diesters) at 20–40° C. The lower aqueous phases is separated off, and the upper pyridine phase (402 g) is diluted with 100 g of toluene and dried by azeotropic distillation. In a subsequent distillation, first the toluene is removed and then the pyridine is distilled over. This results in 360 g of 4-ethyl-2-methylpyridine containing 95.3% (4.6% toluene, 0.07% water). This corresponds to a recovery rate of 94.4% based on pyridine employed.

The pyridine obtained in this way can be employed directly for synthesizing the required O,O'-dialkyl thiophosphate.

Example 3

5-ethyl-2-methylpyridine (160 g, 1.32 mole) and toluene (69 g) were added to a 1-liter, 4-neck flask equipped with an overhead stirrer, a condenser, an addition funnel and a thermometer and were then cooled to 0° C. Thiophosphoryl chloride (74.5 g, 0.44 mole) was added to the mixture while the temperature was kept constant. Isopropyl alcohol (28 g, 0.47 mole) was added dropwise over 1 hour while the reaction temperature was kept at 0° C. The mixture was agitated for 30 minutes. Ethanol (60.5 g, 1.32 mole) was added dropwise and the temperature was kept at less than 10° C. Upon completion of the alcohol addition, the mixture was agitated for 4 hours. The mixture was then drowned in a 15% HCI solution and the O-ethyl, O-isopropylphosphorochloridothioate was recovered from the organic phase. The product yield was 72.1% and product purity was 92%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of an O-alkyl, O-alkyl phosphorochloridothioate comprising:

1) reacting A) a thiophosphoryl halide with B) an alcohol, in the presence of C) a tertiary amine acid acceptor selected from the group consisting of tertiary pyridine bases, tertiary pyrrolidine bases and tertiary pyrolle bases, and D) a solvent, wherein the relative amounts of materials are as follows:
      i) the weight ratio of (D) to (A) is from 1:0.25 to 1:5,
      ii) the molar ratio of (C) to (A) is from 1.5:1 to 5:1, and
      iii) the molar ratio of (A) to (B) is from 1:1 to 1:2, 2) reacting the resultant product with a second alcohol, different from the alcohol used in step 1), wherein the molar ratio of said second alcohol to said thiophosphoryl halide is from 1.5:1 to 5:1.

2. The process of claim 1, wherein the product of step 1) is not isolated before reaction with the second alcohol.

3. The process of claim 1 wherein the thiophosphoryl halide is thiophosphoryl chloride.

4. The process of claim 1 wherein the mole ratio of the tertiary amine acid acceptor C) to the thiophosphoryl halide A) is from about 2.5 to 3.5:1.

5. The process of claim 1 wherein the tertiary amine acid acceptor is selected from the group consisting of pyridine; 2- or 4-picoline; 2,3-, 2,4-, 2,5-, 2,6-, or 3,5-lutidine; 2-ethylpyridine; 5-ethyl- or 4-ethyl-2-methylpyridine; 4-phenylpropylpyridine; 2,3,6- and 2,4,6-collidine; quinoline; isoquinoline; 2,3-cyclopenopyridine; 2,3-cyclohexenopyridine; 1-methylpyrrole; N-methylpyrrolidine; N,N-dimethylpiperazine; N,N-dimethylaniline; N,N-dimethylbenzylamine, triethylamine and tetramethylenediamine.

6. The process of claim 4 wherein the tertiary amine acid acceptor either 5-ethyl- or 4-ethyl-2-methylpyridine.

7. The process of claim 1 wherein the alcohol used in step 1) is isopropyl alcohol.

8. The process of claim 1 wherein the weight ratio of (D) to (A) is from 1:1 to 1.5:1.

9. The process of claim 1 both steps are at a temperature of from about −10 to 50° C.

10. The process of claim 1 wherein said thiophosphoryl halide is thiophosphoryl chloride, said alcohol B) is isopropyl alcohol, said tertiary amine acid acceptor is 5-ethyl- or 4-ethyl-2-methylpyridine, said solvent is toluene and said second alcohol is ethanol.

* * * * *